United States Patent [19]

Weithmann

[11] Patent Number: 4,904,648

[45] Date of Patent: Feb. 27, 1990

[54] PHARMACEUTICAL PREPARATIONS FOR INDUCTION OF LABOR AND FOR CONTRACEPTIVE USE

[75] Inventor: Klaus U. Weithmann, Hofheim am Taunus, Fed. Rep. of Germany

[73] Assignee: Hoechst Aktiengesellschaft, Fed. Rep. of Germany

[21] Appl. No.: 311,257

[22] Filed: Feb. 16, 1989

[30] Foreign Application Priority Data

Feb. 18, 1988 [DE] Fed. Rep. of Germany ....... 3805064

[51] Int. Cl.$^4$ .............................................. A61K 31/56
[52] U.S. Cl. .................................................... 514/171
[58] Field of Search ......................................... 514/171

[56] References Cited

U.S. PATENT DOCUMENTS 4,626,531 12/1986 Elger et al. ......................... 514/171

FOREIGN PATENT DOCUMENTS 0173478 3/1986 European Pat. Off. ............. 514/171

Primary Examiner—Joseph A. Lipovsky
Attorney, Agent, or Firm—Finnegan, Henderson, Farabow, Garrett & Dunner

[57] ABSTRACT

The present invention relates to a pharmaceutical combination product for the induction of labor or for preventing the development of pregnancy, containing (A) one or more antigestagen(s)
(B) one or more long-chain polyunsaturated fatty acid(s) or preparations thereof and, if necessary,
(C) prostaglandins, where suitable as antigestagens are all compounds which have a strong affinity for the gestagen receptor but at the same time do not themselves have any considerable intrinsic gestagenic activity.

The products are preferably administered intravaginally or (extra)amnially. In this connection, it is possible for the antigestagens and the fatty acids according to the invention to be administered either simultaneously or separately, for example consecutively.

16 Claims, No Drawings

PHARMACEUTICAL PREPARATIONS FOR INDUCTION OF LABOR AND FOR CONTRACEPTIVE USE

Pharmacological and surgical methods with whose aid it is possible in mammals and in human medicine to terminate pregnancy prematurely or to induce labor artificially have already been disclosed.

EP-A 139608 describes the state of the art with regard to pharmacological methods. Thus, a termination of pregnancy can be initiated, for example, by medical administration of certain prostaglandins or, alternatively, by administration of antigestagens (antiprogesterones, progesterone antagonists, antiprogestomimetics). The disadvantage of these methods is that they are not one hundred percent reliable. Furthermore, the use of prostaglandins in particular often leads to undesired medical side effects. This is why it is proposed in EP-A 139608 (cf. also EP-A 0184471) to increase the reliability of the method, with at the same time a reduced rate of side effects, by combined administration of prostaglandins and antigestagens.

It is, however, now known that prostaglandins not only have uteroactive effects but also are involved in numerous biological processes. The literature describes the synthesis of prostaglandins in a very wide variety of cell types. They act therein as essential transmitter or modulator substances in biochemical signal transmission and, moreover, are involved in a wide variety of biological reactions such as, for example, of the expression of pain and fever, of the influencing of muscle tone, of the tension in dilator/constrictor muscles of vessels, and of the tendency of the blood to thrombose. Hence, because of this wide variety of biological effects displayed by the prostaglandins, it can be understood that their external medical use, whether systemic or local, brings about not only the desired therapeutic effects in the target cell but also many biological side effects which do not contribute to the medically desired effect and frequently are even injurious. Consequently, the medical administration of prostaglandins according to the state of the art, even with reduced dosages, must be regarded as problematic with regard to the undesired side effects.

It has now been found, according to the present invention, that the prostaglandin-typical side effects of the above-mentioned prostaglandin/antiprogesterone combinations can, surprisingly, be avoided if the prostaglandin content is completely or partly replaced by long-chain polyunsaturated fatty acids or by suitable preparations of such fatty acids (see EP-A 244832). It is particularly important in this connection that these fatty acids, or the fatty acid preparation, are, as a rule, used locally (topically), especially amnially or intravaginally, where appropriate in the form of the transdermal systems known in pharmacy.

When such combinations of antiprogesterone and the said fatty acids (or preparations) are used, the above-mentioned undesired, especially prostaglandin-typical, side effects do not occur, although the reliability of the desired effect is better according to the invention than would be expected on the basis of the additive effect of the individual components. It may be mentioned here that the "desired effect" is to be understood as not only the induction of labor and the induction of termination of pregnancy but also according to the invention the inhibition of nidation of the fertilized ovum.

Hence the present invention relates to pharmaceutical combination products for conjoint use for inducing labor, for terminating pregnancy and for preventing the development of pregnancy, containing (A) one or more antigestagen(s) and (B) one or more long-chain polyunsaturated fatty acid(s) or preparations thereof, and, if necessary, (C) prostaglandins (especially those mentioned in EP-A 139608, page 3–4), where suitable as (A) antigestagens are all compounds which have a strong affinity for the gestagen receptor (progesterone receptor) but do not at the same time show any considerable intrinsic gestagenic activity. Examples of suitable progesterone antagonists are the following steroids:

11$\beta$-[4-(N,N-dimethylamino)phenyl]-17$\beta$-hydroxy-17-propynyl-4,9(10)-estradien-3-one (RU 38 486; see EP-A 139 608)

11$\beta$-[4-(N,N-dimethylamino)phenyl]-17$\beta$-hydroxy-18-methyl-17$\alpha$-propynyl-4,9(10)-estradien-3-one and 11$\beta$-4-[N,N-dimethylamino)phenyl]-17a$\beta$-hydroxy-17a$\alpha$-propynyl-D-homo-4,9(10),16-estratrien-3-one, 17$\beta$-hydroxy-11$\beta$-[4-(N,N-dimethylamino)phenyl]-17$\alpha$-[3-hydroxy-1-propenyl]estra-4,9(10)-dien-3-one, furthermore 11$\beta$-p-methoxyphenyl-17$\beta$-hydroxy-17$\alpha$-ethynyl-4,9(10)-estradien-3-one (Steroids 37 (1981) 361–382) and 11$\beta$-(4-dimethylaminophenyl)-17$\alpha$-hydroxy-17$\beta$-(3-hydroxypropyl)-13$\alpha$-methyl-4,9(10)-gonadien-3-one (see EP-A 139608)

as well as the antigestagens described in EP-A 184471, and as B) long-chain polyunsaturated fatty acids, or the pharmaceutical preparations thereof, such as one or more unsaturated fatty acid(s) having 2, 3, 4 or 5 double bonds which are arranged in isolation, and 18 to 22 carbon atoms which are arranged in a straight chain and can be methylated or ethylated on one or two carbon atoms in positions 2, 3, 4, 16, 17, 18, 19 or 20, as free carboxylic acid with terminal —CO$_2$H or —CO$_2$X, where X represents a protective group which can be eliminated under acidic conditions, such as an alkyl radical, for example a methyl or ethyl radical, or a metal or amine cation or the cationic form of an ion exchanger, or as carboxamide, where appropriate combined with compounds such as (B$_1$) a phenolic compound of the formula I

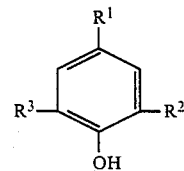

in which the radicals R$^2$ and R$^3$ denote hydroxyl groups or hydrogen, and R$^1$ denotes the radical —OH, —CO$_2$H, —CH$_2$—CO$_2$H, —CH=CH—CO$_2$H, —CH$_2$—CHR$^4$—R$^5$, —CHOH—CH$_2$—NH—R$^6$ with R$^4$=—H or —CO$_2$H and R$^5$=—H or —NH$_2$ and R$^6$=—H, —CH$_3$ or —C$_2$H$_5$, (B$_2$) an indole derivative of the formula II

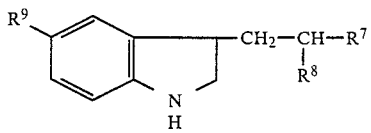

in which $R^7$ denotes hydrogen or COOH, $R^8$ denotes hydrogen or $-NH_2$, and $R^9$ denotes hydrogen, or $-OH$, ($B_3$) cysteine or homocysteine, or liponic acid whose acyclic alkyl radical can be shortened by up to four methylene groups, ($B_4$) a peptide composed of a maximum of ten amino acids, in which one or more of the amino acids has in each case been replaced by one of the compounds specified in ($B_1$) to ($B_3$), ($B_5$) a compound which is specified in ($B_1$) to ($B_4$) and which can carry a $C_1$-$C_4$-alkanoyl grup on a nitrogen atom, ($B_6$) a flavone derivative which is substituted by at least one hydroxyl group which may carry a sugar residue, ($B_7$) a salt of the ionic forms of the compounds specified in ($B_1$)-($B_6$) and, where appropriate, ($B_8$) a carboxylic acid compound which is specified in ($B_1$) to ($B_7$) and which can be esterified with an alkoxy radical or be in the form of a carboxamide, which can also be mono- or dialkylated; and, where appropriate, as stabilizers one or more compounds of the following groups:

($B_9$) dimethyl sulfoxide, ethyl alcohol, glycerol, ethylene glycol, polyethylene glycol or glycerol triacetate, ($B_{10}$) phospholipids, glycolipids, cyclodextrins, proteins, for example those which can be prepared from human or mammalian blood, or vitamins of the E series.

Examples of metal cations X which can be used are those of the alkali metals such as lithium, sodium and potassium, and of the alkaline earth metals such as magnesium and calcium, but also cationic forms of other metals such as aluminum, zinc and iron, where appropriate chelated with citric acid or ethylenediaminetetraacetic acid and the like. Amine cations are those of primary, secondary or tertiary amines such as of the alkylamines, for example mono-, di- and trimethyl- or -ethyl-, -propyl-, -isopropyl-, -butyl-, -isobutyl-, -t-butyl-amine, as well as N-(methylhexyl)-, N-methylhexyl-, benzyl-β-phenyl-ethylamine, ethylenediamine, diethylenetriamine, pyrrolidine, piperidine, morpholine, piperazine, mono-, di- and triethanolamine, ethyldiethanolamine, N-butylethanolamine, tris(hydroxymethyl)aminomethane and the like. Examples of suitable amine salts are those of tryptamine and cysteine, as well as the basic amine salts of lysine and of arginine. Examples of suitable quaternary ammonium cations are tetramethylammonium and benzyltrimethylammonium. These cations can also be used to form salts of the anionic forms of the compounds specified in ($B_1$) to ($B_6$), while, on the other hand, chloride and fluoride are preferred for forming salts in the case of cationic forms.

Preferably used are the fatty acids designated 18:2 ω-6, 20:4, ω-6, 22:5 ω-6, 18:3 ω-3, 20:5 ω-3, 22:6 ω-3, 18:3 ω-6, 20:3 ω-6, 22:3 ω-6, 22:4 ω-6 and 22:4 ω-3, where, in the customary nomenclature, the first figure denotes the number of carbon atoms, the figure after the colon denotes the number of double bonds, and the figure after the omega denotes the position of the first double bond calculated from the methyl end of the molecule. Particularly preferred are the fatty acids 20:4 w-6 and 20:3 w-6.

The antigestagen dosages necessary for the said biological uses in the combination therapy according to the invention are, as a rule, below the dosages necessary in an antigestagen monotherapy. In general, sufficient as a daily dose for human uses are, for example, 10–400 mg of 11β-[4-(N,N-dimethylamino)phenyl]-17β-hydroxy-17α-propynyl-4,9(10)-estradien-3-one (RU 38486, identical to RU 486). Of course, it is possible for RU 38486 to be replaced by biologically equivalent amounts of other antigestagens. Specifically, the dosage which is necessary depends, on the one hand, on the biological response of the person or animal to be treated, which in turn depends on the age, condition etc., and, on the other hand, on the mode of administration, which can take place orally, subcutaneously, enterally or parenterally by means of pills, capsules, coated tablets, tablets, solutions or suspensions etc. Preferred administration is intravaginally (topical or sub- or transcutaneous) or (extra)amnially, which can be carried out, for example by use of vaginal suppositories or transdermal systems such as skin plasters. The pharmaceutical forms contain, as a rule, additives and vehicles according to the state of the art in order to ensure good penetration through the skin. Based on RU 38486, one dosage unit contains 10–200, preferably 50–150, mg, and that for other antigestagens will be calculated according to their biological equivalences.

The administration of the long-chain polyunsaturated fatty acids is effected according to the invention intravaginally (topical, sub- or transcutaneous), for example by vaginal suppositories, or (extra)amnially, where appropriate by transdermal systems and, if necessary, with additives and vehicles according to the state of the pharmaceutical art. The daily dose based on arachidonic acid or dihomogammalinolenic acid is between 1 and 2000 mg, in general between 2 and 1000 mg, and preferably between 5 and 500 mg. The dosage unit contains 1 to 1000, preferably 5 to 500, mg of arachidonic acid (dihomogammalinoleic acid). The dosages necessary for other fatty acids according to the invention can easily be calculated using the extent of their biological effect as cyclooxygenase substrate. It is particularly advantageous to use the fatty acid preparations described above, containing one or more of the compounds $B_1$–$B_{10}$, preferably in the dose ratios specified in EP-A 244 832.

The dosages of all the said active substances should, when used in animals, be lowered or raised according to, in particular, their weight and their biological responses.

The administration of the combination according to the invention often takes place over 1 to 3 or 4, preferably 1 to 2, days and can be repeated where appropriate after 5 to 20 days. In this connection, it is possible for the antigestagens and the fatty acids according to the invention to be used both separately and, preferably, simultaneously, but also consecutively (sequentially) in a ratio by weight of antigestagen to fatty acids of 1:1 to 1:300. A ratio by weight of <1:20, in particular <1:30, is preferred.

For the local (topical) intravaginal or (extra)amnial administration it is advantageous to combine the fatty acid according to the invention and the antigestagen in a dosage unit, for example a suppository. It is possible, if necessary, to choose to delay the release of the fatty acids according to the invention or of the antigestagen from the pharmaceutical form by addition of suitable retarding agents (for example Eudragit ®). The fatty acids according to the invention, or the preparations thereof, can also be contained in separate pharmaceutical units which, however, are combined in a pharmaceutical pack for conjoint use.

EXAMPLES

Example 1

50 mg of 11β-[4-(N,N-dimethylamino)phenyl]-17β-hydroxy-17α-propynyl-4,9(10)-estradien-3-one are dissolved in 30 ml of 96% ethanol. The solution is applied to a commercially available tampon as described in "Fertility and Sterility" 44, (1985) page 263 and is dried at 40° C. To this are applied in an analogous manner 50 ml of a likewise 96% strength ethanol solution which contains 50 mg of dihomogammalinolenic acid and 100 mg of liponic acid, and drying is carried out at a maximum temperature of 30° C.

Example 2

A suppository containing the active substances is prepared by melting 8 g of cocoa butter in a suitable mold with the aid of an IR lamp (maximum temperature=34° C.) and mixing the melt with 50 mg of arachidonic acid and 5 mg of the said antiprogesterone. Some (about 20 mg) flaked solid cocoa butter is added to the melt which is then cooled in a refrigerator. Every effect of moisture, heat and light must be avoided on storage of the suppositories.

Example 3

10 g of an aqueous solution which contains 15% by weight of gelatin and 0.5% by weight of glycerol are cautiously heated in a fusion mold, and the homogeneous composition which forms is mixed, while heating gently, with 20 mg of the abovementioned antiprogesterone, 30 mg of dihomogammalinolenic acid and, if necessary, with 30 mg of N-acetylcysteamine, until homogeneous, and is finally cooled.

Example 4

A film contains: 0.72 mg of polyoxyethylene/polyoxypropylene polymer (Pluronic F 68 ®), 41 mg of hydroxypropylcellulose and 100 mg sodium arachidonate. The film is uniformly coated with a suspension composed of 100 mg of cocoa butter and 10 mg of 11β-[4-(N,N-dimethylamino)-phenyl]-17β-hydroxy-17α-propynyl-4,9(10)-estradien-3-one.

Example 5

Determination of the uterine synthesis of prostaglandin F2alpha

Female Wistar rats (about 150 g) were treated s.c. with 30 mcg of beta-estradiol diacetate and sacrificed the next day, the uteri were removed and homogenized in 7.3 ml of 50 mmol/l potassium phosphate buffer (pH=8) with the addition of 6 mg/l $^{14}$C-arachidonic acid, and centrifugation and one wash with buffer were carried out. The active substances indicated in Tab. 1 were added in each case to 250 mcl of the resulting suspension and then incubated at 37° C. for 30 min. The reaction was stopped using 50 mcl of 1.2 mol/l citric acid and then the mixture was extracted twice with 0.75 ml of ethyl acetate each time, the ester was blown off with nitrogen, and the residue was dissolved in 0.1 ml of methanol. The products which had formed were fractionated by high-pressure liquid chromatography as described in detail in EP 0244832, page 18. The peak area was used to quantify prostaglandin F2alpha.

| Experiment No. | Addition of | Rel. amount of prostaglandin F2alpha | % Increase over control |
|---|---|---|---|
| I | none | 243 | 0 |
| II | 3 mg/l progesterone | 289 | 18.9 |
| III | 3 mg/l RU 38486 | 314 | 29.6 |
| IV | 3 mg/l progesterone plus 3 mg/l RU 38486 | 400 | 64.6 |

The synthesis of prostaglandin F2alpha was stimulated by addition of progesterone (see % increase column), and the increase was even more pronounced after addition of RU 38486 and of the combination of progesterone and RU 38486. The synthesis of prostaglandin F2alpha was additionally increased by 150% by addition of the thiol compound glutathione. A similar stimulation was also measured after increasing the amount of arachidonic acid added to 30 mg/l. A further increase in the synthesis rate by about 30% was achieved by addition of 75 mg/l arachidonic acid. The increase in stimulation was less pronounced with larger amounts of arachidonic acid. Accordingly, a favorable ratio by weight of antiprogesterone to polyunsaturated fatty acid is about 1:10 to 1:25. When the ratio by weight becomes less than 1:100 the synthesis rate for prostaglandin F2alpha increases only slowly.

Example 6

The uterine tone, or the uterine contractility, is determined not only by prostaglandin F2alpha but also by the cyclic AMP level in the tissue, see Nature, Vol. 225 (Jan. 17, 1970), page 282.

Determination of cyclic AMP in the uterus

Uterus homogenate is prepared as described in Example 5 from rats treated with beta-estradiol diacetate. The buffer used for the homogenization is composed of 0.14 mol/l NaCl, 5 mmol/l KCl, 10 mmol/l glucose, 10 mmol/l acetic acid, 2 mmol/l disodium hydrogen phosphate, 20 mmol/l tris-HCl, 0.001% phenol red, 1.2 mol/l MgSO$_4$, 0.8 mmol/l CaCl$_2$ and 0.01 mmol/l isobutylmethylxanthine. Before use, this buffer is brought to pH 7.4 by passing in CO$_2$ gas. 10 ml of the uterus homogenate are now incubated with 0.3 mmol/l tritiated adenine at 37° C. for 40 minutes. The tissue is now filtered, again taken up in the above buffer, and subsequently divided up in such a way that each portion is suspended in 10 ml of the said buffer. After a preincubation period of 5 minutes, the active substances specified in Tab. 2 are added, and the mixture is incubated for a further 100 minutes. It is then filtered again, the tissue is deep-frozen in liquid nitrogen and crushed, and the resulting powder is homogenized in 1 ml of 6% strength trichloroacetic acid. Cyclic AMP is subsequently separated out and quantified by column chromatography as in Analytical Biochemistry 58, (1974) 541–548 (in particular Method C, page 543). Tab. 2 shows the results:

| Experiment | Addition | Cyclic AMP (% conversion) | Difference from the control |
|---|---|---|---|
| I | none (control) | 0.53 | — |
| II | 2 mmol/l arachidonic acid | 1.06 | 0.53 |
| III | 3 mmol/l dihomogamma- linolenic acid | 1.45 | 0.92 |
| IV | 0.1 mmol/l RU 38486 | 0.92 | 0.39 |
| V | 0.1 mmol/l RU 38486 plus 3 mmol/l arachidonic acid | 2.49 | 1.96 |
| VI | 0.1 mmol/l RU 38486 plus 3 mmol/l dihomogamma- linolenic acid | 3.19 | 2.66 |
| VII | 0.1 mmol/l RU 38486 plus 3 mmol/l eicosapentaenoic acid (20:5 ω-3) | 0.95 | 0.42 |

It emerged as the result, in particular, that the combination of antiprogesterone with dihomogammalinolenic acid is able even more effectively to influence uterine contractility via the cyclic AMP level that is the combination with arachidonic acid (Experiments V and VI), whereas eicosapentaenoic acid (20:5/ω-3) was virtually ineffective (Experiment VII).

| VIII | 0.1 mmol/l RU 38486 plus 3 mmol/l dihomogamma- linolenic acid plus 0.2 mcmol/l prostaglandin $E_1$ | 3,52 | 2,99 |
|---|---|---|---|

An additional stimulation of the uterine contractility via the cyclic AMP level can be achieved by addition of a little prostaglandin $E_1$ (Experiment VIII).

I claim:

1. A pharmaceutical composition useful as a contraceptive and in the induction of labor comprising a therapeutically effective amount of at least one antigestagen and one or more long-chain fatty acids.

2. The composition of claim 1 further comprising at least one prostaglandin.

3. The composition of claim 1 further comprising stabilizers, stimulators of prostaglandin synthesis or combinations thereof.

4. The composition of claim 2 further comprising stabilizers, stimulators of prostaglandin synthesis or combinations thereof.

5. The composition of claim 1 wherein the anti-gestagen is selected from the group consisting of
11β-[4-(N,N-dimethylamino)phenyl]-17β-hydroxy-17α-propynyl-4,9(10)-estradien-3-one,
11β-[4-(N,N-dimethylamino)phenyl]-17β-hydroxy-18-methyl-17α-propynyl-4,9(10)-estradien-3-one,
11β-[4-(N,N-dimethylamino)phenyl]-17αβ-hydroxy-17aα-propynyl D-homo-4,9(10), 16-estratrien-3-one,
11β-p-methoxyphenyl 17β-hydroxy-17α-ethynyl-4 9(10)-estradien-3-one and
11β-(4-dimethylaminophenyl)-17β-hydroxy-17β-(3-hydroxy-propyl)-13α methyl 4,9(10)-gonadien-3-one.

6. The composition of claim 1 wherein the long-chain fatty acids contain 3 to 5 double bonds which are arranged in isolation, and 18 to 22 carbon atoms which are arranged in a straight chain and which can be methylated or ethylated on one or two carbon atoms in positions 2, 3, 4, 16, 17, 18, 19 or 20, and which have the end group —$CO_2X$, where X represents hydrogen, the amino group, a protective group which can be eliminated under acidic conditions a metal or amino cation or the cationic form of an ion exchanger.

7. The composition of claim 6 wherein the long-chain fatty acids are selected from the group consisting of 18:2 ω-6, 20:4 ω-6, 22:5 ω-6, 18:3 ω-3, 20:5 ω-3, 22:6 ω-3, 18:3 ω-6, 20:3 ω-6, 22:3 ω-6, 22:4 ω-6 and 22:4 ω-3.

8. The composition of claim 1 wherein the long-chain fatty acid is selected from the group consisting of arachidonic acid and dihomogammalinolenic acid.

9. The composition of claim 2 wherein the prostaglandins are of the E or F series.

10. The composition of claim 1 wherein the antigestagens and polyunsaturated fatty acids are present in a ratio by weight of 1:1 to 1:300.

11. The composition of claim 1 wherein the antigestagens and polyunsaturated fatty acids are present in a ratio by weight of less than 1 part to 20.

12. The composition of claim 1 which contains 1–500 mg of a long-chain polyunsaturated fatty acid per dosage unit.

13. A method of inducing labor, terminating pregnancy or preventing conception comprising administering to a mammal in need thereof a therapeutically effective amount of the composition of claim 1.

14. A method of inducing labor, terminating pregnancy or preventing contraception comprising administering to a mammal in need thereof a therapeutically effective amount of the composition of claim 2.

15. A method of inducing labor, terminating pregnancy or preventing contraception comprising administering to a mammal in need thereof a therapeutically effective amount of the composition of claim 3.

16. A method of inducing labor, terminating pregnancy or preventing contraception comprising administering to a mammal in need thereof a therapeutically effective amount of the composition of claim 4.

* * * * *